United States Patent
Brown et al.

(10) Patent No.: US 10,406,157 B2
(45) Date of Patent: Sep. 10, 2019

(54) TETRAHYDROPYRIDOPYRAZINE MODULATORS OF GPR6

(71) Applicant: Takeda Pharmaceutical Company Limited, Osaka-shi (JP)

(72) Inventors: Jason W. Brown, San Diego, CA (US); Stephen Hitchcock, San Diego, CA (US); Maria Hopkins, San Diego, CA (US); Shota Kikuchi, San Diego, CA (US); Holger Monenschein, San Diego, CA (US); Holly Reichard, San Diego, CA (US); Kristin Schleicher, San Diego, CA (US); Huikai Sun, San Diego, CA (US); Todd Macklin, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/009,308

(22) Filed: Jun. 15, 2018

(65) Prior Publication Data

US 2018/0360831 A1    Dec. 20, 2018

Related U.S. Application Data

(60) Provisional application No. 62/520,430, filed on Jun. 15, 2017, provisional application No. 62/591,247, filed on Nov. 28, 2017, provisional application No. 62/649,856, filed on Mar. 29, 2018, provisional application No. 62/672,261, filed on May 16, 2018.

(51) Int. Cl.
*A61K 31/4985* (2006.01)
*A61K 45/06* (2006.01)
*C07D 487/04* (2006.01)
*A61P 9/00* (2006.01)
*A61P 25/16* (2006.01)

(52) U.S. Cl.
CPC .......... *A61K 31/4985* (2013.01); *A61K 45/06* (2013.01); *A61P 9/00* (2018.01); *A61P 25/16* (2018.01); *C07D 487/04* (2013.01)

(58) Field of Classification Search
USPC ........................................................ 544/350
See application file for complete search history.

(56) References Cited

U.S. PATENT DOCUMENTS

| | | | |
|---|---|---|---|
| 6,106,864 A | 8/2000 | Dolan et al. | |
| 7,229,557 B2 | 6/2007 | Krsek et al. | |
| 9,181,249 B2 * | 11/2015 | Brown | C07D 471/04 |
| 9,708,313 B2 * | 7/2017 | Brown | C07D 471/04 |
| 10,077,266 B2 * | 9/2018 | Brown | C07D 471/04 |
| 2012/0101106 A1 | 1/2012 | Mercer et al. | |
| 2015/0175602 A1 | 6/2015 | Brown et al. | |

FOREIGN PATENT DOCUMENTS

| | | |
|---|---|---|
| WO | WO 1991/011172 A1 | 8/1991 |
| WO | WO 1994/002518 A1 | 2/1994 |
| WO | WO 1998/055148 A1 | 12/1998 |
| WO | WO2015/095728 A1 | 6/2015 |
| WO | 2015/123505 | 8/2015 |

OTHER PUBLICATIONS

X. Yao et al., "Predicting QT prolongation in humans during early drug development using hERG inhibition and an anaesthetized guinea-pig model," British Journal of Pharmacology (2008) 154:1446-56.
S. M. Berge et al., "Pharmaceutical Salts", Journal of Pharmaceutical Sciences (1977) 66:1-19.
O. Almarsson and M. J. Zaworotko, "Crystal engineering of the composition of pharmaceutical phases. Do pharmaceutical co-crystals represent a new path to improved medicines?", Chemical Communications (2004) 17:1889-1896.
J. K. Haleblian, "Characterization of habits and crystalline modification of solids and their pharmaceutical applications" Journal of Pharmaceutical Sciences (1975) 64(8):1269-88.
T. Higuchi and V. Stella "Pro drugs as Novel Delivery Systems," ACS Symposium Series 14 (1975).
Verma et al, "Current Status of Drug Delivery Technologies and Future Directions" Pharmaceutical Technology On-line (2001) 25(2):1-14.
Finnin and Morgan, "Transdermal Penetration Enhancers: Applications, Limitations, and Potential" Journal of Pharmaceutical Sciences 88(10):955 958 (1999).
Duty, S. & Jenner, P. Br. J. Pharmacol. 164:1357-1391 (2011).
Liang, et al., "Fast-dissolving intraoral drug delivery systems", Expert Opin. in Ther. Patents (2001), 11(6), pp. 981-986.

(Continued)

*Primary Examiner* — Nyeemah A Grazier
(74) *Attorney, Agent, or Firm* — Barnes & Thornburg LLP; Scott D. Rothenberger

(57) ABSTRACT

Disclosed is a compound of Formula 1,

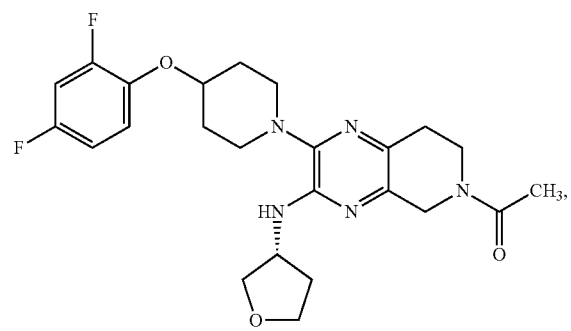

and a pharmaceutically acceptable salt thereof. This disclosure also relates to materials and methods for preparing the compound of Formula 1, to pharmaceutical compositions which contain it, and to its use for treating diseases, disorders, and conditions associated with GPR6.

28 Claims, 1 Drawing Sheet

(56) References Cited

OTHER PUBLICATIONS

Haleblian, J.K., "Characterization of Habits and Crystalline Modification of Solids and Their Pharamaceutical Applications", Journal of Pharmaceutical Sciences, Aug. 1975, vol. 64, No. 8, pp. 1269-1288.
Higuchi, T., et al. "Pro-drugs as Novel Delivery Systems", ACS Symposium Series 14 (1975).
International Search Report and Written Opinion, dated Aug. 28, 2018, for PCT Application No. PCT/US2018/037687, filed Jun. 15, 2018.

* cited by examiner

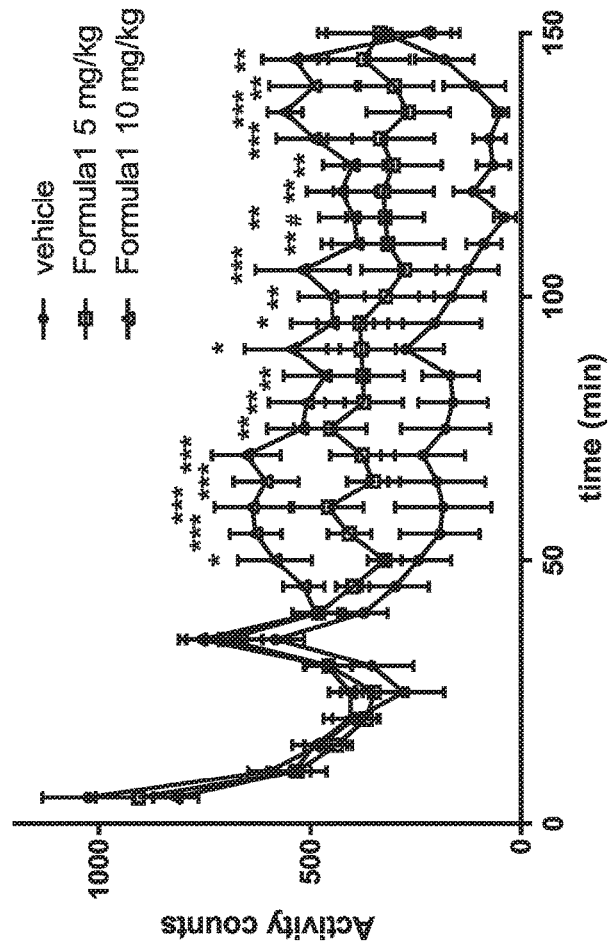

TETRAHYDROPYRIDOPYRAZINE MODULATORS OF GPR6

CROSS-REFERENCE TO RELATED APPLICATIONS

This application claims the benefit of U.S. provisional application 62/520,430 filed Jun. 15, 2017; U.S. provisional application 62/591,247 filed Nov. 28, 2017; U.S. provisional application 62/649,856 filed Mar. 29, 2018; and U.S. provisional application 62/672,261 filed May 16, 2018; each of which is hereby incorporated by reference in its entirety.

FIELD OF THE INVENTION

This invention relates to tetrahydropyridopyrazine derivatives which are modulators of G protein-coupled receptor 6 (GPR6), to pharmaceutical compositions which contain them, and to their use to treat diseases, disorders, and conditions associated with GPR6.

BACKGROUND OF THE INVENTION

GPR6 is a member of the G protein-coupled receptor (GPCR) family of transmembrane receptors. GPR6 signals through the G protein (Gs) pathway. It is highly expressed in the central nervous system (CNS), particularly in medium spiny neurons (MSNs) of the striatum and exhibits minimal expression in peripheral tissues. The major striatal targets of dopaminergic innervation reside in the MSNs of the striatopallidal (indirect) and striatonigral (direct) output pathways. The MSNs of the direct output pathway express D1 dopamine receptors while those in the indirect pathway express D2 receptors. GPR6 is enriched in the D2 receptor-expressing MSNs of the striatum where GPR6 activity increases the levels of intracellular second messenger cAMP, which is functionally opposed to D2 receptor signaling. Antagonism or inverse agonism of Gs-coupled GPR6 decreases cAMP in MSNs and thus provides a functional alternative to dopamine-mediated activation of D2 receptors.

Published international patent application WO 2015/095728A1, which is hereby incorporated by reference in its entirety, describes a number of tetrahydropyridopyrazine derivatives, which are modulators of GPR6. These compounds include (S)-1-(2-(4-(2,4-difluorophenoxy)piperidin-1-yl)-3-((tetrahydrofuran-3-yl)amino)-7,8-dihydropyrido[3,4-b]pyrazin-6(5H)-yl)ethan-1-one ("Compound A"). Though Compound A is a potentially efficacious modulator of GPR6, it had a suboptimal safety margin relative to inhibition of hERG (human ether-a-go-go-related gene) activity. See e.g., X. Yao et al., *British Journal of Pharmacology* (2008) 154:1446-56. Inhibition of hERG is one factor associated with potential QT interval prolongation and cardiac arrhythmia.

SUMMARY OF THE INVENTION

This invention provides a tetrahydropyridopyrazine derivative and pharmaceutical compositions which contain it. The tetrahydropyridopyrazine derivative is a modulator of GPR6 and may be used to treat diseases, disorders, and conditions associated with GPR6, including neurological disorders such as Parkinson's disease.

One aspect of the invention provides a compound of Formula 1:

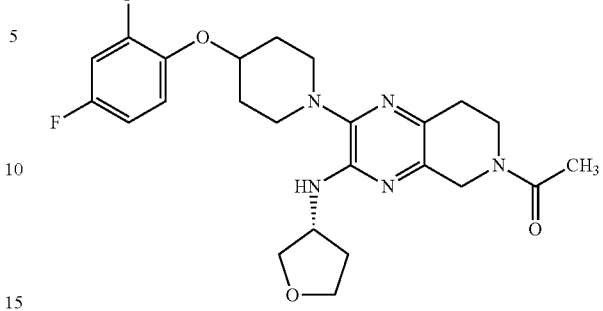

or a pharmaceutically acceptable salt thereof. Formula 1 depicts the compound (R)-1-(2-(4-(2,4-difluorophenoxy)piperidin-1-yl)-3-((tetrahydrofuran-3-yl)amino)-7,8-dihydropyrido[3,4-b]pyrazin-6(5H)-yl)ethan-1-one.

In certain embodiments, the compound or pharmaceutically acceptable salt of Formula 1 has an enantiomeric purity equal to or greater than 20% enantiomeric excess (ee), 40% ee, 60% ee, 80% ee, 90% ee, 98% ee, 99% ee, or 100% ee. In certain embodiments, the compound is present as a free form.

A further aspect of the invention provides a pharmaceutical composition which includes a compound of Formula 1 or a pharmaceutically acceptable salt thereof as described herein; and a pharmaceutically acceptable excipient.

An additional aspect of the invention provides a pharmaceutical composition comprising a compound of Formula 1 or a pharmaceutically acceptable salt thereof as described herein for use as a medicament. In certain embodiments, the pharmaceutical composition is for use in the treatment Parkinson's disease, levodopa-induced dyskinesias, Huntington's disease, drug addiction, eating disorders, cognitive disorders, schizophrenia, bipolar disorder, epilepsy, Alzheimer's disease, anxiety, and depression. In certain embodiments, the pharmaceutical composition further comprises amantadine. Another aspect of the invention provides the pharmaceutical composition for use as a treatment of a disease, disorder or condition associated with GPR6.

Various embodiments of the invention described herein provide a pharmaceutical composition comprising a compound of Formula 1 or a pharmaceutically acceptable salt thereof as described herein, and a pharmaceutically acceptable excipient. In certain embodiments, the pharmaceutical composition is for use as a medicament. In certain embodiments, the use of the pharmaceutical composition is treatment of a disease, disorder, or condition is selected from the group consisting of: Parkinson's disease, levodopa-induced dyskinesias, Huntington's disease, drug addiction, eating disorders, cognitive disorders, schizophrenia, bipolar disorder, epilepsy, Alzheimer's disease, anxiety, and depression.

A further aspect of the invention provides a use of a compound of Formula 1 or a pharmaceutically acceptable salt thereof for the manufacture of a medicament for the treatment of a disease, disorder or condition associated with GPR6. In certain embodiments, the disease, disorder, or condition is selected from the group consisting of: Parkinson's disease, levodopa-induced dyskinesias, Huntington's disease, drug addiction, eating disorders, cognitive disorders, schizophrenia, bipolar disorder, epilepsy, Alzheimer's disease, anxiety, and depression.

An additional aspect of the invention provides a method of treating a disease, disorder or condition associated with GPR6, the method comprising administering to the subject an effective amount of a compound of Formula 1 or a pharmaceutically acceptable salt thereof as described herein. In certain embodiments, the compound of Formula 1 or a pharmaceutically acceptable salt thereof is administered perorally.

Another aspect of the invention provides a method of treating a disease, disorder or condition in a subject, the method comprising administering to the subject an effective amount of the compound of Formula 1 or pharmaceutically acceptable salt thereof, wherein the disease, disorder or condition is selected from Parkinson's disease, levodopa-induced dyskinesias, Huntington's disease, drug addiction, eating disorders, cognitive disorders, schizophrenia, bipolar disorder, epilepsy, Alzheimer's disease, anxiety, and depression.

In certain embodiments, the compound of Formula 1 or a pharmaceutically acceptable salt thereof administered in the method described herein is administered at a dose selected from a range of about 0.1 mg/kg to about 1.0 mg/kg or about 0.5 mg/kg to about 5.0 mg/kg. In certain embodiments, the compound or pharmaceutically acceptable salt is administered at a dose within the range of about 40 mg/kg to about 60 mg/kg. In certain embodiments, the compound of Formula 1 or a pharmaceutically acceptable salt thereof administered in the method described herein is administered at a dose selected from a range in the group consisting of: about 5 mg/kg to about 15 mg/kg, about 10 mg/kg to about 20 mg/kg, about 15 mg/kg to about 25 mg/kg, about 20 to about 30 mg/kg, about 25 mg/kg to about 35 mg/kg, about 30 mg/kg to about 40 mg/kg, about 35 mg/kg to about 45 mg/kg, and about 45 mg/kg to about 55 mg/kg. In certain embodiments, the dose is in a range selected from the group consisting of: about 30 mg/kg to about 40 mg/kg, about 35 mg/kg to about 45 mg/kg, about 40 mg/kg to about 50 mg/kg, about 45 mg/kg to about 55 mg/kg, about 50 mg/kg to about 60 mg/kg, about 55 mg/kg to about 65 mg/kg, and about 60 mg/kg to about 70 mg/kg. In certain embodiments, the dose may be about 50 mg/kg. In certain embodiments, the dose is greater than about 1 mg/kg. In certain embodiments, the dose is about 1 mg/kg. In certain embodiments, the dose is within a range selected from the group consisting of: about 50 mg/kg to about 100 mg/kg, about 100 mg/kg to about 150 mg/kg, about 150 mg/kg to about 200 mg/kg, about 200 mg/kg to about 250 mg/kg, about 250 mg/kg to about 350 mg/kg, about 300 mg/kg to about 350 mg/kg, about 350 mg/kg to about 400 mg/kg, about 400 mg/kg to about 450 mg/kg, about 450 mg/kg to about 500 mg/g. In certain embodiments, the dose is about 500 mg/kg. Alternatively, the dose is less than 500 mg/kg.

In certain embodiments, the dose is 35 mg/kg. In certain embodiments, the dose is 36 mg/kg. In certain embodiments, the dose is 37 mg/kg. In certain embodiments, the dose is 38 mg/kg. In certain embodiments, the dose is 39 mg/kg. In certain embodiments, the dose is 40 mg/kg. In certain embodiments, the dose is 41 mg/kg. In certain embodiments, the dose is 42 mg/kg. In certain embodiments, the dose is 43 mg/kg. In certain embodiments, the dose is 44 mg/kg. In certain embodiments, the dose is 45 mg/kg. In certain embodiments, the dose is 46 mg/kg. In certain embodiments, the dose is 47 mg/kg. In certain embodiments, the dose is 48 mg/kg. In certain embodiments, the dose is 49 mg/kg. In certain embodiments, the dose is 50 mg/kg. In certain embodiments, the dose is 51 mg/kg. In certain embodiments, the dose is 52 mg/kg. In certain embodiments, the dose is 53 mg/kg. In certain embodiments, the dose is 54 mg/kg. In certain embodiments, the dose is 55 mg/kg. In certain embodiments, the dose is 56 mg/kg. In certain embodiments, the dose is 57 mg/kg. In certain embodiments, the dose is 58 mg/kg. In certain embodiments, the dose is 59 mg/kg. In certain embodiments, the dose is 60 mg/kg. In certain embodiments, the dose is 61 mg/kg. In certain embodiments, the dose is 62 mg/kg. In certain embodiments, the dose is 63 mg/kg. In certain embodiments, the dose is 64 mg/kg. In certain embodiments, the dose is 65 mg/kg. In certain embodiments, the administering step occurs orally.

A further aspect of the invention provides a combination therapy comprises an effective amount of the pharmaceutical composition; and at least one additional pharmacologically active agent. In certain embodiments, the additional pharmacologically active agent is selected from the group consisting of: levodopa, a DOPA decarboxylase inhibitor, a dopamine agonist, an anticholinergic, a B-selective monoamine oxidase inhibitor, and a catechol O-methyl transferase inhibitor. In other embodiments, the additional pharmacologically active agent is levodopa in combination with a DOPA decarboxylase inhibitor. In certain embodiments, the additional pharmacologically active agent is selected from the group consisting of: carbidopa; benserazid; methyldopa; α-difluoromethyl-DOPA; 3',4',5,7-tetrahydroxy-8-methoxyisoflavone; apomorphine hydrochloride; bromocriptine; rotigotine; pramipexole; ropinirole; trihexyphenidyl; benztropine mesylate; safinamide; selegiline; rasagiline; entacapone; and tolcapone. In certain embodiments, the additional pharmacologically active agent is selected from the group consisting of: beta-secretase inhibitors, gamma-secretase inhibitors, HMG-CoA reductase inhibitors, nonsteroidal anti-inflammatory drugs (NSAIDs). In certain embodiments, the additional pharmacologically active agent is selected from the group consisting of: apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac. In certain embodiments, the additional pharmacologically active agent is selected from the group consisting of: donepezil, rivastigmine, memantine, and galantamine. In certain embodiments, the additional pharmacologically active agent is selected from the group consisting of: sedatives, hypnotics, anxiolytics, antipsychotics, and tranquilizers. In certain embodiments, the additional pharmacologically active agent is selected from the group consisting of: amitriptyline, amoxapine, aripiprazole, asenapine, bupropion, chlordiazepoxide, citalopram, chlorpromazine, clozapine, desipramine, desvenlafaxine, doxepin, duloxetine, escitalopram, fluoxetine, fluoxetine, fluphenazine, haloperidol, iloperidone, imipramine, isocarboxazid, lamotrigine, levomilnacipran, lurasidone, mirtazapine, nefazodone, nortriptyline, olanzapine, paliperidone, paroxetine, perphenazine, phenelzine, protriptyline, quetiapine, risperidone, safinamide, selegiline, sertraline, tranylcypromine, trazodone, trimipramine, venlafaxine, vilazodone, vortioxetine, and ziprasidone. In certain embodiments, the additional pharmacologically active agent is selected from the group consisting of: alprazolam, chlordiazepoxide, clobazepam, clonazepam, clorazepate, diazepam, estazolam, flurazepam, lorazepam, midazolam, oxazepam, prazepam, quazepam, temazepam, and triazolam, hydroxyzine, eszopiclone, zaleplon, zolpidem, and zopiclone, and buspirone. In certain embodiments, the additional pharmacologically active agent is selected from the group consisting of: acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide Various embodiments of the invention herein provide a method of treating Parkinson's disease in a subject comprising: administering the pharmaceutical composition as defined herein to the subject. In some embodiments, administering the pharmaceutical composition improves the motoric symptoms of the subject. In certain embodiments, the administering step is performed orally.

Various embodiments of the invention herein provide a dosage form of the compound of Formula 1 or a pharmaceutically acceptable salt thereof adapted for oral administration of the compound or a pharmaceutically acceptable salt at a dose selected from a range in the group consisting of: about a range of about 0.1 mg/kg to about 1.0 mg/kg or about 0.5 mg/kg to about 5.0 mg/kg. In certain embodiments, the compound or pharmaceutically acceptable salt is administered at a dose within the range of about 40 mg/kg to about 60 mg/kg. In certain embodiments, the compound of Formula 1 or a pharmaceutically acceptable salt thereof is in a dose selected from a range in the group consisting of: about 5 mg/kg to about 15 mg/kg, about 10 mg/kg to about 20 mg/kg, about 15 mg/kg to about 25 mg/kg, about 20 to about 30 mg/kg, about 25 mg/kg to about 35 mg/kg, about 30 mg/kg to about 40 mg/kg, about 35 mg/kg to about 45 mg/kg, and about 45 mg/kg to about 55 mg/kg. In certain embodiments, the dose is in a range selected from the group consisting of: about 30 mg/kg to about 40 mg/kg, about 35 mg/kg to about 45 mg/kg, about 40 mg/kg to about 50 mg/kg, about 45 mg/kg to about 55 mg/kg, about 50 mg/kg to about 60 mg/kg, about 55 mg/kg to about 65 mg/kg, and about 60 mg/kg to about 70 mg/kg. In certain embodiments, the dose may be about 50 mg/kg. In certain embodiments, the dose is greater than about 1 mg/kg. In certain embodiments, the dose is about 1 mg/kg. In certain embodiments, the dose is within a range selected from the group consisting of: about 50 mg/kg to about 100 mg/kg, about 100 mg/kg to about 150 mg/kg, about 150 mg/kg to about 200 mg/kg, about 200 mg/kg to about 250 mg/kg, about 250 mg/kg to about 350 mg/kg, about 300 mg/kg to about 350 mg/kg, about 350 mg/kg to about 400 mg/kg, about 400 mg/kg to about 450 mg/kg, about 450 mg/kg to about 500 mg/g. In certain embodiments, the dose is about 500 mg/kg. Alternatively, the dose is less than 500 mg/kg.

In certain embodiments, the dose is 35 mg/kg. In certain embodiments, the dose is 36 mg/kg. In certain embodiments, the dose is 37 mg/kg. In certain embodiments, the dose is 38 mg/kg. In certain embodiments, the dose is 39 mg/kg. In certain embodiments, the dose is 40 mg/kg. In certain embodiments, the dose is 41 mg/kg. In certain embodiments, the dose is 42 mg/kg. In certain embodiments, the dose is 43 mg/kg. In certain embodiments, the dose is 44 mg/kg. In certain embodiments, the dose is 45 mg/kg. In certain embodiments, the dose is 46 mg/kg. In certain embodiments, the dose is 47 mg/kg. In certain embodiments, the dose is 48 mg/kg. In certain embodiments, the dose is 49 mg/kg. In certain embodiments, the dose is 50 mg/kg. In certain embodiments, the dose is 51 mg/kg. In certain embodiments, the dose is 52 mg/kg. In certain embodiments, the dose is 53 mg/kg. In certain embodiments, the dose is 54 mg/kg. In certain embodiments, the dose is 55 mg/kg. In certain embodiments, the dose is 56 mg/kg. In certain embodiments, the dose is 57 mg/kg. In certain embodiments, the dose is 58 mg/kg. In certain embodiments, the dose is 59 mg/kg. In certain embodiments, the dose is 60 mg/kg. In certain embodiments, the dose is 61 mg/kg. In certain embodiments, the dose is 62 mg/kg. In certain embodiments, the dose is 63 mg/kg. In certain embodiments, the dose is 64 mg/kg. In certain embodiments, the dose is 65 mg/kg.

BRIEF DESCRIPTION OF THE DRAWINGS

The foregoing and other objects, features and advantages will be apparent from the following description of particular embodiments of the invention, as illustrated in the accompanying drawings. The drawings are not necessarily to scale; emphasis instead being placed upon illustrating the principles of various embodiments of the invention.

FIG. 1 is a graph showing the effect of the treatment on the 6-hydroxydopamine (6-OHDA) model of Parkinson's disease.

DETAILED DESCRIPTION OF THE INVENTION

This application is related to WO 2015/095728, which is hereby incorporated by reference in its entirety.

I. Definitions

Unless otherwise indicated, this disclosure uses definitions provided below.

"About" or "approximately," when used in connection with a measurable numerical variable, refers to the indicated value of the variable and to all values of the variable that are within the experimental error of the indicated value or within ±10 percent of the indicated value, whichever is greater.

"Enantiomeric excess" or "ee" refers to the excess of one enantiomer over the other, expressed as a percentage of the whole, and is a measure of the enantiomeric (chiral) purity of a sample which contains the enantiomer. For example, if a sample contains excess R-enantiomer, then ee may be determined from the expression $$ee = \frac{A_R - A_S}{A_R + A_S} \times 100$$

where $A_R$ and $A_S$ are the amounts of the R- and S-enantiomers in the sample.

"Combination therapy" refers to an approach for treatment of a disease, disorder, or condition that includes more than one therapeutic modality. For example, the therapeutic modalities may be more than one pharmaceutical composition or pharmaceutically active agent or a combination thereof. The therapeutic modalities may be administered simultaneously, sequentially, or at any order. They may be administered at different dosages, with different dosing frequencies, or via different routes, whichever is suitable. The molar ratio of the therapeutic modalities is not particularly restricted.

"Motoric symptoms" refer to the decrease in activity occurring in a subject with a disease, disorder, and condition associated with GPR6, such as Parkinson's disease.

"Substantially pure enantiomer" and variants thereof refer to an enantiomer which is present in a sample at 90% ee or greater.

"Pure enantiomer" and variants thereof refer to an enantiomer which is present in a sample at 98% ee or greater.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compound of Formula 1) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with GPR6" and similar phrases relate to a disease, disorder or condition in a subject for which modulation GPR6, including antagonism or inverse agonism of GPR6, may provide a therapeutic or prophylactic benefit.

The following abbreviations may be used in the specification: Ac (acetyl); ACN (acetonitrile); AIBN (azo-bisisobutyronitrile); API (active pharmaceutical ingredient); aq (aqueous); BINAP (2,2'-bis(diphenylphosphino)-1,1'-binaphthyl); Boc (tert-butoxycarbonyl); Cbz (carbobenzyloxy); dba (dibenzylideneacetone); DCC (1,3-dicyclohexylcarbodiimide); DCE (1,1-dichloroethane); DCM (dichloromethane); DIPEA (N,N-diisopropylethylamine, Hünig's Base); DMA (N,N-dimethylacetamide); DMAP (4-dimethylaminopyridine); DME (1,2-dimethoxyethane); DMF (N,N-dimethylformamide); DMSO (dimethylsulfoxide); dppf (1,1'-bis(diphenylphosphino)ferrocene); DTT (dithiothreitol); $EC_{50}$ (effective concentration at half maximal response); EDA (ethoxylated dodecyl alcohol, BRIJ® 35); EDC (N-(3-dimethylaminopropyl)-N'-ethylcarbodiimide); EDTA (ethylenediaminetetraacetic acid); ee (enantiomeric excess); eq (equivalents); Et (ethyl); $Et_3N$ (triethyl-amine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); HOAc (acetic acid); HOBt (1H-benzo[d][1,2,3]triazol-1-01); $IC_{50}$ (concentration at 50% inhibition); IPA (isopropanol); iPrOAc (isopropyl acetate); IPE (isopropylether); Ki (inhibition constant; concentration of a competing ligand in a competition assay which would occupy 50% of the receptors if no ligand were present); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); NMP (N-methyl-pyrrolidone); OTf (triflate); PE (petroleum ether); Ph (phenyl); $pEC_{50}$ ($-\log_{10}(EC_{50})$, where $EC_{50}$ is given in molar (M) units); $pIC_{50}$ ($-\log_{10}(IC_{50})$, where $IC_{50}$ is given in molar (M) units); Pr (propyl); c-Pr (cyclopropyl), i-Pr (isopropyl); PTFE (polytetrafluoroethylene); RT (room temperature, approximately 20° C. to 25° C.); T3P (2,4,6-tripropyl-1,3,5,2,4,6-trioxatriphosphinane 2,4,6-trioxide); TCEP (tris(2-carboxyethyl)phosphine); TFA (trifluoroacetic acid); TFAA (2,2,2-trifluoroacetic anhydride); THF (tetrahydrofuran); TMEDA ($N^1,N^1,N^2,N^2$-tetramethylethane-1,2-diamine); TMS (trimethylsilyl); and Tris buffer (2-amino-2-hydroxymethyl-propane-1,3-diol buffer).

II. Compositions of the Invention

As described, below, this disclosure concerns a compound of Formula 1 and its pharmaceutically acceptable salts. This disclosure also concerns materials and methods for preparing the compound of Formula 1, pharmaceutical compositions which contain it, and the use of the compound of Formula 1 and its pharmaceutically acceptable salts (optionally in combination with other pharmacologically active agents) for treating diseases, disorders or conditions of the CNS, including Parkinson's disease, and other diseases, disorders or conditions associated with GPR6.

The compound of Formula 1 may exist as a salt, complex, solvate, hydrate, and liquid crystal. Likewise, a salt of the compound of Formula 1 may exist as a complex, solvate, hydrate, and liquid crystal.

The compound of Formula 1 may form a pharmaceutically acceptable salt. These salts include acid addition salts (including di-acids) and base salts. Pharmaceutically acceptable acid addition salts may include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts may include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts may include salts derived from bases, including metal cations, such as an alkali or alkaline earth metal cation, as well as amines. Examples of suitable metal cations may include sodium, potassium, magnesium, calcium, zinc, and aluminum. Examples of suitable amines may include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see, S. M. Berge et al., *J. Pharm. Sci.* (1977) 66:1-19; see also Stahl and Wermuth, *Handbook of Pharmaceutical Salts: Properties, Selection, and Use* (2002); both of which are hereby incorporated by reference in their entireties.

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

The compound of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

The compound of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995), which is hereby incorporated by reference in its entirety. Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

The compound of Formula 1 may also exist as a multi-component complex (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896, which is hereby incorporated by reference in its entirety. For a general review of multi-component complexes, see J. K. Haleblian, *J. Pharm. Sci.* (1975) 64(8): 1269-88, which is hereby incorporated by reference in its entirety.

When subjected to suitable conditions, the compound of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., —COO$^-$Na$^+$, —COO$^-$K$^+$, —SO$_3^-$Na$^+$) or polar non-ionic moiety (such as —N$^-$N$^+$(CH$_3$)$_3$). See, e.g., N. H. Hartshorne and A. Stuart, *Crystals and the Polarizing Microscope* (4th ed, 1970), which is hereby incorporated by reference in its entirety.

The compound of Formula 1 may exist as polymorphs, may be isotopically-labeled, may result from the administration of a prodrug, or may form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985), which is hereby incorporated by reference in its entirety. Examples of prodrugs include ester, ether or amide derivatives of the compound of Formula 1 having carboxylic acid, hydroxy, or amino functional groups, respectively. For further discussions of prodrugs, see e.g., T. Higuchi and V. Stella "Prodrugs as Novel Delivery Systems," *ACS Symposium Series* 14 (1975) and E. B. Roche ed., *Bioreversible Carriers in Drug Design* (1987), each of which is hereby incorporated by reference in its entirety.

"Metabolites" refer to compounds formed in vivo upon administration of pharmacologically active compounds. Examples include hydroxymethyl, hydroxy, secondary amino, primary amino, phenol, and carboxylic acid derivatives of the compound of Formula 1 having methyl, alkoxy, tertiary amino, secondary amino, phenyl, and amide groups, respectively.

The compound of Formula 1 may possess isotopic variations, in which at least one atom is replaced by an atom having the same atomic number, but an atomic mass different from the atomic mass usually found in nature. Isotopes suitable for inclusion in the compound of Formula 1 include, for example, isotopes of hydrogen, such as $^2H$ and $^3H$; isotopes of carbon, such as $^{11}C$, $^{13}C$ and $^{14}C$; isotopes of nitrogen, such as $^{13}N$ and $^{15}N$; isotopes of oxygen, such as $^{15}O$, $^{17}O$ and $^{18}O$; and isotopes of fluorine, such as $^{18}F$. Use of isotopic variations (e.g., deuterium, 41) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3H$, or $^{14}C$), which may be useful in drug and/or substrate tissue distribution studies. Substitution with positron emitting isotopes, such as $^{11}C$, $^{18}F$, $^{15}O$ and $^{13}N$, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

III. Methods of Making the Composition of the Invention

The compound of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999) and the multi-volume series edited by Michael B. Smith and others, *Compendium of Organic Synthetic Methods* (1974 et seq.), each of which is hereby incorporated by reference in its entirety. Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts; *Protective Groups in Organic Chemistry*; $3^{rd}$ edition; John Wiley & Sons, Inc.; New York (1999) and P. Kocienski, *Protective Groups*, Georg Thieme, Stuttgart (2000), each of which is hereby incorporated by reference in its entirety.

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure and claims to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane, cyclohexane, methylcyclohexane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

IV. Formulations and Administration

The compound of Formula 1, which includes its pharmaceutically acceptable complexes, salts, solvates and hydrates, should be assessed for biopharmaceutical properties, such as solubility and solution stability across pH, permeability, and the like, to select an appropriate dosage form and route of administration. A compound intended for pharmaceutical use may be administered as a crystalline or amorphous product, and may be obtained, for example, as solid plugs, powders, or films by methods such as precipitation, crystallization, freeze drying, spray drying, evaporative drying, microwave drying, or radio frequency drying.

The compound of Formula 1 may be administered alone or in combination with one or more pharmacologically active compounds. Generally, one or more of these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

The compound of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

The compound of Formula 1 may also be used in fast-dissolving, fast-disintegrating dosage forms such as those described in Liang and Chen, *Expert Opinion in Therapeutic Patents* (2001) 11(6):981-986, which is hereby incorporated by reference in its entirety.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets, Vol.* 1-3 (2d ed., 1990); and D. K. Parikh & C. K. Parikh, *Handbook of Pharmaceutical Granulation Technology, Vol.* 81 (1997), each of which is hereby incorporated by reference in its entirety.

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may be carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864, which is hereby incorporated by reference in its entirety. For details of other useful release technologies, such as high energy dispersions and osmotic and coated particles, see, Verma et al, *Pharmaceutical Technology On-line* (2001) 25(2):1-14, which is hereby incorporated by reference in its entirety.

The compound of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, the compound of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, the compound of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

The compound of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10): 955-958 (1999), which is hereby incorporated by reference in its entirety.

Other means of topical administration include delivery by electroporation, iontophoresis, phonophoresis, sonophoresis and microneedle or needle-free (e.g. POWDERJECT™ and BIOJECT™) injection. Formulations for topical administration may be formulated to be immediate or modified release as described above.

The compound of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 µg to about 20 mg of the API per actuation and the actuation volume may vary from about 1 µL to about 100 µL. A typical formulation may comprise the compound of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 m of the API. The overall daily dose will typically range from about 1 mg/kg to about 500 mg/kg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

The compound of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, the compound of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 1991/011172, WO 1994/002518, and WO 1998/055148, each of which is hereby incorporated by reference in its entirety.

As noted above, the compound of Formula 1, including its pharmaceutically acceptable complexes, salts, solvates and hydrates, may be combined with one or more other active pharmaceutically active compounds to treat various diseases, disorders, and conditions. In such cases, the active compounds may be combined in a single dosage form as described above or may be provided in the form of a kit which is suitable for coadministration of the compositions. The kit comprises (1) two or more different pharmaceutical compositions, at least one of which contains the compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed compound is typically in the range of about a range of about 0.1 mg/kg to about 1.0 mg/kg or about 0.5 mg/kg to about 5.0 mg/kg. In certain embodiments, the compound or pharmaceutically acceptable salt is administered at a dose within the range of about 40 mg/kg to about 60 mg/kg. In certain embodiments, the compound of Formula 1 or a pharmaceutically acceptable salt thereof administered in the method described herein is administered at a dose selected from a range in the group consisting of: about 5 mg/kg to about 15 mg/kg, about 10 mg/kg to about 20 mg/kg, about 15 mg/kg to about 25 mg/kg, about 20 to about 30 mg/kg, about 25 mg/kg to about 35 mg/kg, about 30 mg/kg to about 40 mg/kg, about 35 mg/kg to about 45 mg/kg, and about 45 mg/kg to about 55 mg/kg. In certain embodiments, the dose is in a range selected from the group consisting of: about 30 mg/kg to about 40 mg/kg, about 35 mg/kg to about 45 mg/kg, about 40 mg/kg to about 50 mg/kg, about 45 mg/kg to about 55 mg/kg, about 50 mg/kg to about 60 mg/kg, about 55 mg/kg to about 65 mg/kg, and about 60 mg/kg to about 70 mg/kg. In certain embodiments, the dose may be about 50 mg/kg. In certain embodiments, the dose is greater than about 1 mg/kg. In certain embodiments, the dose is about 1 mg/kg. In certain embodiments, the dose is within a range selected from the group consisting of: about 50 mg/kg to about 100 mg/kg, about 100 mg/kg to about 150 mg/kg, about 150 mg/kg to about 200 mg/kg, about 200 mg/kg to about 250 mg/kg, about 250 mg/kg to about 350 mg/kg, about 300 mg/kg to about 350 mg/kg, about 350 mg/kg to about 400 mg/kg, about 400 mg/kg to about 450 mg/kg, about 450 mg/kg to about 500 mg/g. In certain embodiments, the dose is about 500 mg/kg. Alternatively, the dose is less than 500 mg/kg.

In certain embodiments, the dose is 35 mg/kg. In certain embodiments, the dose is 36 mg/kg. In certain embodiments, the dose is 37 mg/kg. In certain embodiments, the dose is 38 mg/kg. In certain embodiments, the dose is 39 mg/kg. In certain embodiments, the dose is 40 mg/kg. In certain embodiments, the dose is 41 mg/kg. In certain embodiments, the dose is 42 mg/kg. In certain embodiments, the dose is 43 mg/kg. In certain embodiments, the dose is 44 mg/kg. In certain embodiments, the dose is 45 mg/kg. In certain embodiments, the dose is 46 mg/kg. In certain embodiments, the dose is 47 mg/kg. In certain embodiments, the dose is 48 mg/kg. In certain embodiments, the dose is 49 mg/kg. In certain embodiments, the dose is 50 mg/kg. In certain embodiments, the dose is 51 mg/kg. In certain embodiments, the dose is 52 mg/kg. In certain embodiments, the dose is 53 mg/kg. In certain embodiments, the dose is 54 mg/kg. In certain embodiments, the dose is 55 mg/kg. In certain embodiments, the dose is 56 mg/kg. In certain embodiments, the dose is 57 mg/kg. In certain embodiments, the dose is 58 mg/kg. In certain embodiments, the dose is 59 mg/kg. In certain embodiments, the dose is 60 mg/kg. In certain embodiments, the dose is 61 mg/kg. In certain embodiments, the dose is 62 mg/kg. In certain embodiments, the dose is 63 mg/kg. In certain embodiments, the dose is 64 mg/kg. In certain embodiments, the dose is 65 mg/kg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., pediatric patient) whose mass falls outside of this mass range.

The compound of Formula 1 may be used to treat diseases, disorders, and conditions for which modulation of GPR6 is indicated. As mentioned above, antagonism or inverse agonism of Gs-coupled GPR6 provides a functional alternative to dopamine-mediated activation of D2 receptors. As such, compounds that modulate the activity of GPR6 may be useful for treating a variety of neurological and psychiatric disorders, including movement disorders such as Parkinson's disease, levodopa-induced dyskinesias, and Huntington's disease, as well as drug addiction, eating disorders, cognitive disorders, schizophrenia, bipolar disorder, epilepsy, and depression. In certain embodiments, the compound of Formula 1 improves the motoric symptoms of a subject to treat Parkinson's disease. In certain embodiments, the compound of Formula 1 is included in a combination therapy with amantadine for treatment of these disorders.

The pathological hallmark of Parkinson disease is neuronal cell loss within the substantia nigra. Degeneration of the nigrostriatal pathway causes reduction in the striatal concentration of dopamine which results in motor and nonmotor clinical manifestations. Many Parkinson's disease patients are treated with levodopa, a prodrug for dopamine. Levodopa has common serious side effects including induced dyskinesia (LID), impulsive control disorders (ICD), psychotic symptoms and sleep disturbances. LID is a progressive disease, with about 90% of Parkinson's disease patients developing LID within 10 years. Irreversible adaptations occur in D1 receptor signaling in MSNs in rodent models of LID, including reduced desensitization leading to hypersensitivity in the direct pathway. Genetic inactivation of D1 but not D2 receptors abolishes LID in mice. However, blockade of D1 receptor signaling does not affect the antiparkinsonian efficacy of levodopa. The 6-OHDA model mimics many aspects of Parkinson's disease including loss of dopamine neurotransmission and motor impairments.

The claimed compound may be combined with one or more other pharmacologically active compounds or therapies to treat one or more diseases, disorders or conditions associated with GPR6. Such combinations may offer significant therapeutic advantages, including fewer side effects, improved ability to treat undeserved patient populations, or synergistic activity. For example, the compound of Formula 1, which includes its pharmaceutically acceptable complexes, salts, solvates and hydrates, may be administered simultaneously, sequentially or separately in combination with one or more compounds or therapies for treating movement disorders, including Parkinson's disease. These compounds include levodopa; DOPA decarboxylase inhibitors such as carbidopa, benserazid, methyldopa, α-difluoromethyl-DOPA, and 3',4',5,7-tetrahydroxy-8-methoxyisoflavone; dopamine agonists, such as apomorphine hydrochloride, bromocriptine, rotigotine, pramipexole, and ropinirole; amantadine; anticholinergics, such as trihexyphenidyl and benztropine mesylate; B-selective monoamine oxidase (MAO-B) inhibitors, such as safinamide, selegiline, and rasagiline; and catechol O-methyl transferase (COMT) inhibitors, such as entacapone and tolcapone.

In addition to drugs used to treat movement disorders, the compound of Formula 1 may be combined with medications used to treat Alzheimer's disease and other diseases, disorders, and conditions affecting cognition. Such medications include beta-secretase inhibitors, gamma-secretase inhibitors, HMG-CoA reductase inhibitors, nonsteroidal anti-inflammatory drugs (NSAIDs, such as apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac), vitamin E, and anti-amyloid antibodies. Specific examples of compounds used to treat Alzheimer's disease include donepezil, rivastigmine, memantine, and galantamine.

Additionally or alternatively, the compound of Formula 1 may be combined with sedatives, hypnotics, anxiolytics, antipsychotics, tranquilizers, and other medications that are used in the treatment of neurological or psychiatric diseases. For example, the compound of Formula 1 may be combined with one or more agents for treating depression (antidepressants) and/or schizophrenia (atypical or typical antipsychotics) including amitriptyline, amoxapine, aripiprazole, asenapine, bupropion, chlordiazepoxide, citalopram, chlorpromazine, clozapine, desipramine, desvenlafaxine, doxepin, duloxetine, escitalopram, fluoxetine, fluoxetine, fluphenazine, haloperidol, iloperidone, imipramine, isocarboxazid, lamotrigine, levomilnacipran, lurasidone, mirtazapine, nefazodone, nortriptyline, olanzapine, paliperidone, paroxetine, perphenazine, phenelzine, protriptyline, quetiapine, risperidone, selegiline, sertraline, tranylcypromine, trazodone, trimipramine, venlafaxine, vilazodone, and vortioxetine, and ziprasidone.

Likewise, the compound of Formula 1 may be combined with one or more agents for treating anxiety (anxiolytics) including benzodiazepines (alprazolam, chlordiazepoxide, clobazepam, clonazepam, clorazepate, diazepam, estazolam, flurazepam, lorazepam, midazolam, oxazepam, prazepam, quazepam, temazepam, and triazolam), antihistamines (hydroxyzine), non-benzodiazepines (eszopiclone, zaleplon, zolpidem, and zopiclone) and buspirone.

The compound of Formula 1 may also be combined with one or more agents for treating epilepsy (antiepileptics or anticonvulsants) including acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

Biological Activity

The activity of compounds as GPR6 modulators may be determined by a variety of methods, including in vitro and in vivo methods.

I. In Vitro Inhibition of cAMP (EC50)

This cell-based assay measures the ability of test compounds to inhibit the constitutive cAMP activity of GPR6 receptor expressed in CHO-K1 cells. CHO cells are stably expressed with GPR6 receptor, whose expression is controlled by a tetracycline inducible element. The cells were cultured in medium containing F12K, 10% FBS, 1% Penn/Strep, 200 µg/mL Hygromycin. GPR6 receptor expression is induced for 20 hours with 2 µg/mL doxycycline (Sigma D9891) in growth media. After addition of doxycycline, the cells are plated at a density of 450-750 cells per well in 96-well half-volume black tissue culture plates (Costar) and placed in an incubator (37° C., 5% $CO_2$) for 20 hours prior to cAMP assays.

Culture media is removed from the cells and they are washed with 50 µL/well of Ringer's Buffer ($MgCl_2$ 0.047 mg/mL, $NaH_2PO_4$ 0.18 mg/mL, $Na_2HPO_4$ 0.1 mg/mL, KCl 0.34 mg/mL, $NaHCO_3$ 1.26 mg/mL, D-glucose 1.8 mg/mL, NaCl 7 mg/mL; pH=7.4). The test compounds are suspended in DMSO, diluted in Ringer's Buffer containing 0.5% fatty acid free BSA plus 300 µM 3-isobutyl-1-methylxanthine (IBMX), and incubated on the cells for 45 minutes at 37° C. and 5% $CO_2$. After incubation, the cells are conditioned for 10 minutes at room temperature with Eu-cAMP tracer solution from a PerkinElmer LANCE® Ultra cAMP assay kit (TRF0263). Then ULIGHT™-anti-cAMP solution from the LANCE® kit is added and incubated on a shaker at room temperature for 1 hour prior to homogeneous time resolved fluorescence (HTRF) detection in a PerkinElmer EnVision plate reader. $EC_{50}$ curves are generated with a four-parameter logistic equation using GraphPad Prism 5.03.

II. In Vitro Inhibition of cAMP (IC50)

This cell-based assay also measures the ability of compounds to inhibit the constitutive cAMP activity of GPR6 receptor expressed in CHO-K1 cells. CHO cells are stably expressed with GPR6 receptor, whose expression is controlled by a tetracycline inducible element. The cells are cultured in medium containing F12K, 10% FBS, 1% Penn/Strep, 200 µg/mL Hygromycin. GPR6 receptor expression is induced for 20 hours with 1 µg/mL doxycycline (Sigma D9891) in growth media. After addition of doxycycline, cells are plated at a density of 250-500 cells per well in half-volume black clear bottom plates (Costar) and place in an incubator (37° C., 5% $CO_2$) for 20 hours prior to cAMP assays.

Culture media is removed from cells and they are washed with 50 µL of Ringer's Buffer ($MgCl_2$ 0.047 mg/mL, $NaH_2PO_4$ 0.18 mg/mL, $Na_2HPO_4$ 0.1 mg/mL, KCl 0.34 mg/mL, $NaHCO_3$ 1.26 mg/mL, D-glucose 1.8 mg/mL, NaCl 7 mg/mL; pH=7.4). Compounds suspended in DMSO are diluted in Ringer's Buffer containing 0.5% fatty acid free BSA and incubated on cells for 45 minutes at 37° C. and 5% $CO_2$. After incubation, cells are incubated for 10 minutes at room temperature with Eu-cAMP tracer solution from a PerkinElmer LANCE® Ultra cAMP assay kit (TRF0264). Then, ULIGHT™-anti-cAMP solution from the LANCE® kit is added and incubated on a shaker at room temperature for 1 hour prior to HTRF detection in a BMG POLARSTAR® Omega plate reader. IC50 curves were generated with a four-parameter logistic equation using GraphPad Prism 5.03.

III. In Vitro Competition Binding to GPR6 (Ki)

A competition binding assay using a filtration-based format is used to study the binding characteristics of GPR6 inverse agonists. The method employs membranes prepared from CHO-K1 cells expressing human GPR6 cDNA driven by a doxycycline inducible promoter. Assay ready 96 well plates (651201, Greiner, USA) containing serial dilutions of test compounds (1 µL of test ligand/well) are prepared in DMSO using liquid handlers (5 µM, final assay top concentration). Assay buffer (50 mM Tris, pH 7.4, 50 mM NaCl, 6 mM $MgCl_2$, fatty acid free 0.1% BSA, 1:100 proteinase inhibitor cocktail, Sigma USA) is added (39 µL/well) and the plates are mixed on a plate shaker for 10 minutes. GPR6-specific $^3H$ radioligand is prepared in assay buffer and is added to each well (40 µL, 2.4 nM final assay concentration).

To initiate the binding reactions, 40 μL of total membranes obtained from cells expressing human GPR6 receptors is added. The membranes are prepared in assay buffer and added per well to 15 μg/well final assay concentration. The plates are sealed, mixed for 30 seconds at 300 RPM and incubated for 2 hours at room temperature. The reaction mixtures are subsequently filtered through filtermates (1450-421, filtermate A, PerkinElmer, USA) and washed 5 times with buffer (50 mM Tris, pH 7.4, 50 mM NaCl, 6 mM $MgCl_2$, fatty acid free 0.1% BSA) using a Tomtec HARVESTER96™ instrument. The filters are dried in a microwave. Scintillator sheet (1450-411, PerkinElmer, USA) is melted on filters and heat-sealed before CPM/well were quantified in MICROBETA® Trilux instrument (PerkinElmer, USA). Before use, the filtermates are presoaked in 0.5% polyethylenimine solution for 3 hours with gentle shaking, followed by air drying over night. The $IC_{50}$ and Ki values are calculated using non-linear regression analysis in Prism (GraphPad, USA). Kd values are determined in standard radioligand saturation experiments.

IV. In Vivo Parkinson's Disease Model—Haloperidol-Induced Catalepsy

The motor symptoms of Parkinson's disease include akinesia, bradykinesia, rigidity, tremor and postural abnormalities and are associated with the loss of nigral dopaminergic cells and a decline in striatal dopamine levels. Administration of haloperidol to rodents leads to a transient Parkinsonian-like state that is reversed by the administration of levodopa and other drugs that have been clinically validated for the treatment of Parkinson's disease. See Duty, S. & Jenner, P. Br. J. Pharmacol. 164:1357-1391 (2011), which is hereby incorporated by reference in its entirety. Haloperidol antagonizes dopamine D2, and to a lesser extent, D1 receptors in medium spiny neurons that comprise the indirect and direct pathways of the motor circuit, respectively. The resultant block of striatal dopamine transmission results in abnormal downstream firing within the basal ganglia circuits that is manifest as symptoms of muscle rigidity and catalepsy. Catalepsy has been postulated to reflect the clinical features of Parkinson's disease, whereby patients experience an inability to initiate movements.

Male C57Bl6 mice weighing 25-35 g are used. Catalepsy is induced by the subcutaneous (sc) administration of the dopamine receptor antagonist haloperidol (0.45 mg/kg) at least 30 minutes before testing the animals on a vertical grid test. For this test, the rats or mice are placed on a wire mesh cover of a 25 cm×43 cm plexiglass cage placed at an angle of about 70 degrees with the bench table. The subject is placed on the grid with all four legs abducted and extended ("frog posture"). The use of such an unnatural posture is essential for the specificity of this test for catalepsy. The time span from placement of the paws until the first complete removal of one paw (descent latency) is measured maximally for 120 seconds for rats. For mice, the front paws of the mouse are placed on a horizontal metal bar raised 2" above a Plexiglas platform and time is recorded for up to 30 seconds per trial. The test ends when the animal's front paws return to the platform or after 30 seconds. The test is repeated three times and the average of the three trials is reported as the intensity index of catalepsy. Animals evaluated at 30 minutes after dosing are reevaluated at 60 or 90 minutes post dosing of haloperidol.

Efficacy of GPR6 modulators to reverse haloperidol induced catalepsy is measured 30 minutes, 60 minutes, and/or 90 minutes after dosing the subjects with 0.45 mg/kg ip (intraperitoneal injection) of haloperidol along with the GPR6 modulator test compound. The compound of Formula 1 is administered in a dose range from 0.1 to 100 mg/kg (orally/po in 0.5% methyl cellulose) in conjunction with haloperidol. The adenosine A2A antagonist SCH 420814 (preladenant) is dosed at 3 mg/kg ip as a positive control.

V. Inhibition of Human hERG Via Patch Clamp Technique

An automated whole cell patch-clamp system (QPATCH® 16) is used to record outward potassium currents from a single cell. The assay employs CHO-K1 (Chinese Hamster Ovary) cells stably transfected with human hERG cDNA. The cells are harvested by trypsinization and maintained in serum-free medium at room temperature before recording. The cells are washed and re-suspended in the extracellular solution before being applied to the automated patch-clamp sites. The test solutions are prepared in the aqueous extracellular solution (137 mM NaCl, 4 mM KCl, 1.8 mM $CaCl_2$, 1 mM $MgCl_2$, 10 mM D(+)-Glucose, 10 mM HEPES, pH adjusted to 7.4 with NaOH) on the day of patch-clamp assay. Seven concentrations (0.03, 0.1, 0.3, 1, 3, 10, and 30 μM) of the test compound are used to determine IC50. The aqueous intracellular solution contains 130 mM KCl, 10 mM NaCl, 1 mM $MgCl_2$, 10 mM EGTA, 5 mM MgATP, and 10 mM HEPES (pH adjusted to 7.2 with KOH).

After whole cell configuration is achieved, the cell is held at −80 mV. A 50 ms pulse to −40 mV is delivered to measure the leaking current, which is subtracted from the tail current on-line. Then the cell is depolarized to +20 mV for 2 seconds, followed by a 1 second pulse to −40 mV to reveal the hERG tail current. This paradigm is delivered once every 5 seconds to monitor the current amplitude. The assay is conducted at room temperature. The extracellular solution (control) is applied first and the cell is stabilized in the solution for 5 minutes. Then the test compound is applied from low to high concentrations sequentially on the same cell. The cells are incubated with each test concentration for 5 minutes. A reference compound E-4031 (N-(4-(1-(2-(6-methylpyridin-2-yl)ethyl)piperidine-4-carbonyl)phenyl) methanesulfonamide) is tested concurrently at multiple concentrations to obtain an IC50 value. The percent inhibition of hERG channel is calculated by comparing the tail current amplitude before and after application of the compound (the current difference is normalized to the control).

EXAMPLES

The following examples are intended to be illustrative and non-limiting and represent specific embodiments of the present invention.

I. $^1$H Nuclear Magnetic Resonance (NMR)

$^1$H NMR spectra were obtained for many of the compounds in the following examples.

Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), $CD_3OD$ (deuteromethanol), $CD_3CN$ (deuteroacetonitrile), and THF-$d_8$ (deuterotetrahydrofuran). The mass spectra (m/z for [M+H]$^+$) were recorded using either electrospray ionization (ESI-MS) or atmospheric pressure chemical ionization (APCI-MS) mass spectrometry.

II. High-Performance Liquid Chromatography (HPLC)

Where indicated, products of certain preparations and examples are purified by mass-triggered HPLC (e.g., Pump:

WATER™ 2525; MS: ZQ™; Software: MASSLYNX™), flash chromatography or preparative thin layer chromatography (TLC). Reverse phase chromatography is typically carried out on a column (e.g., Phenomenex GEMINI™ 5μ, C18, 30 mm×150 mm; AXIA™, 5μ, 30 mm×75 mm) under acidic conditions ("acid mode") eluting with CH$_3$CN and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM NH$_4$HCO$_3$. Preparative TLC is typically carried out on silica gel 60 F$_{254}$ plates. After isolation by chromatography, the solvent is removed, and the product is obtained by drying in a centrifugal evaporator (e.g., GeneVac™), rotary evaporator, evacuated flask, etc. Reactions in an inert (e.g., nitrogen) or reactive (e.g., H$_2$) atmosphere are typically carried out at a pressure of about 1 atmosphere (14.7 psi).

III. Synthesis

Preparation 1: (R)-2-(4-(2,4-difluorophenoxy)piperidin-1-yl)-N-(tetrahydrofuran-3-yl)pyrido[3,4-b]pyrazin-3-amine

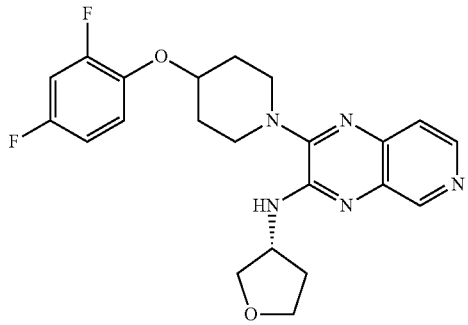 [SMILES: Fc1ccc(OC2CCN(c3nc4ccncc4nc3N[C@@H]3CCOC3)CC2)c(F)c1]

To a solution of 3-chloro-2-(4-(2,4-difluorophenoxy)piperidin-1-yl)pyrido[3,4-b]pyrazine (10 g, 26.5 mmol) in DMSO (50 mL) was added (R)-tetrahydrofuran-3-amine (ArkPharm, AK-75910, Lot WZG082316-PB01) (5.32 mL, 61.0 mmol). The solution was heated at 70° C. for 10 hours, then diluted with water (300 mL) and extracted with iPrOAc (300 mL). The aqueous phase was further extracted with iPrOAc (100 mL). The organic layers were combined, washed with saturated aqueous NH$_4$Cl (300 mL) and with brine (200 mL), dried over MgSO$_4$, concentrated in vacuo and dried under house vacuum to give a light yellow solid (11.4 g). The solid was dissolved in iPrOAc (55 mL) with stirring and heating to reflux. Heptane (33 mL) was added slowly and in portions with heating to prevent precipitation. The solution was then allowed to cool to 20° C. with stirring (ca. 400 rpm) during which time a precipitate formed. The mixture cooled slowly to ambient temperature and was stirred overnight. The solid was collected by vacuum filtration, rinsed with ice-cold 20% iPrOAc in heptane, dried by pulling vacuum through the filter cake for at least 30 minutes, and collected to give the title compound as a light yellow solid (9.771 g, 86%). $^1$H NMR (500 MHz, DMSO-d$_6$) δ ppm 1.84-1.96 (m, 2H), 2.01-2.16 (m, 3H), 2.20-2.31 (m, 1H), 3.22-3.31 (m, 2H), 3.64-3.80 (m, 4H), 3.85-3.93 (m, 1H), 4.00 (dd, J=9.28, 6.35 Hz, 1H), 4.55-4.67 (m, 2H), 6.94 (d, J=5.86 Hz, 1H), 6.99-7.06 (m, 1H), 7.25-7.37 (m, 2H), 7.46 (d, J=5.37 Hz, 1H), 8.31 (d, J=5.37 Hz, 1H), 8.79 (s, 1H); ESI-MS m/z [M+H]$^+$ 428.

Preparation 2: (S)-2-(4-(2,4-difluorophenoxy)piperidin-1-yl)-N-(tetrahydrofuran-3-yl)pyrido[3,4-b]pyrazin-3-amine

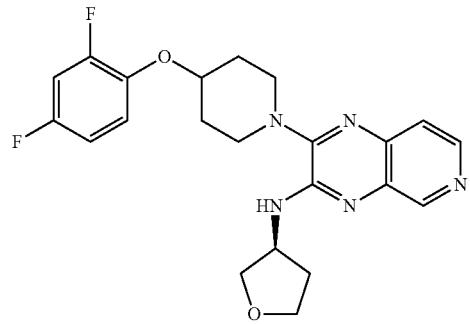 [SMILES: Fc1ccc(OC2CCN(c3nc4ccncc4nc3N[C@H]3CCOC3)CC2)c(F)c1]

To a solution of 3-chloro-2-(4-(2,4-difluorophenoxy)piperidin-1-yl)pyrido[3,4-b]pyrazine (1.0 g, 2.65 mmol) in DMSO (5 mL) was added (S)-tetrahydrofuran-3-amine (AstaTech catalog #37021) (0.578 mL, 6.64 mmol). The solution was heated at 70° C. in a sealed microwave vial for 22 hours at which time HPLC-MS showed the reaction was complete. The reaction mixture (5 mL) was diluted with water (150 mL) and extracted with iPrOAc (150 mL). The aqueous phase was further extracted with iPrOAc (50 mL). The organic layers were combined, washed with saturated aqueous NH$_4$Cl (150 mL) and with brine (100 mL), dried over MgSO$_4$, and concentrated in vacuo on CELITE®. The crude product was purified by column chromatography (30 g NH silica gel column) eluting with a gradient of 0 to 60% EtOAc in heptane to give the title compound as a white solid (1.05 g, 93%). $^1$H NMR (500 MHz, DMSO-d$_6$) δ ppm 1.90 (td, J=8.54, 3.91 Hz, 2H), 2.01-2.16 (m, 3H), 2.20-2.31 (m, 1H), 3.21-3.32 (m, 2H), 3.63-3.80 (m, 4H), 3.89 (q, J=7.49 Hz, 1H), 4.00 (dd, J=9.28, 6.35 Hz, 1H), 4.54-4.67 (m, 2H), 6.96 (d, J=6.35 Hz, 1H), 7.00-7.08 (m, 1H), 7.26-7.39 (m, 2H), 7.46 (d, J=5.37 Hz, 1H), 8.31 (d, J=5.37 Hz, 1H), 8.79 (s, 1H); ESI-MS m/z [M+H]$^+$ 428.

Example 1: (R)-1-(2-(4-(2,4-difluorophenoxy)piperidin-1-yl)-3-((tetrahydrofuran-3-yl)amino)-7,8-dihydropyrido[3,4-b]pyrazin-6(5H)-yl)ethan-1-one

1

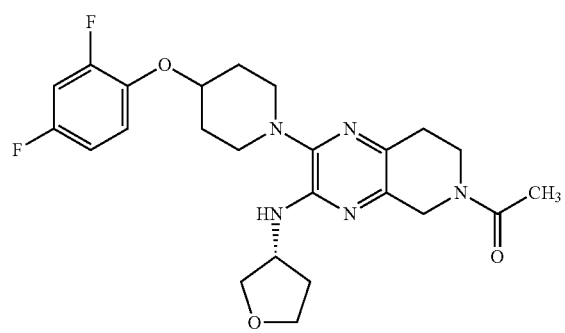

To a flask charged with (R)-2-(4-(2,4-difluorophenoxy)piperidin-1-yl)-N-(tetrahydrofuran-3-yl)pyrido[3,4-b]pyrazin-3-amine (16 g, 37.4 mmol) in HOAc (80 mL) and THF (80 mL) was added acetic anhydride (17.66 mL, 187 mmol) under nitrogen. Palladium on carbon (10%, Aldrich 205699-10G, Lot #MKBZ3284V) (3.19 g, 2.99 mmol) was added under nitrogen. The flask was connected to a hydrogen-filled balloon and was evacuated with house vacuum and refilled with hydrogen eight times. The reaction mixture was stirred under hydrogen for 40 hours and then filtered through a pad of CELITE®, taking care not to let the cake dry out. The flask and filter cake were rinsed with EtOAc (48 mL), methanol (48 mL) and EtOAc (48 mL). The filtrate was concentrated in vacuo to remove THF, EtOAc and methanol (bath temperature ≤40° C.). The solution was diluted with heptane (480 mL) and reconcentrated in vacuo to azetrope off HOAc (bath temperature ≤45° C.). The residue was taken up in iPrOAc (320 mL), washed with 10 wt % aqueous $K_2CO_3$ (320 mL, 230 mmol) (pH 13 before wash, pH 10 after wash) and brine (240 mL, pH 7 after wash), dried over $MgSO_4$, concentrated in vacuo and dried under house vacuum for at least 1 hour to give a light yellow solid (16.71 g). The crude product was taken up in ethanol (84 mL) and was heated in an oil bath with stirring. After the solids were dissolved, the solution was allowed to cool slowly in the oil bath with stirring, during which a precipitate started to form, and the solution became cloudy. The mixture was allowed to cool to ambient temperature in the oil bath and was stirred overnight. Following recrystallization, the white solid was collected by vacuum filtration, rinsed with ice-cold ethanol, and dried under high vacuum to give the title compound as a white solid (13.34 g, 75%). $^1$H NMR (500 MHz, DMSO-$d_6$) δ ppm 1.81-2.00 (m, 3H), 2.02-2.12 (m, 5H), 2.14-2.24 (m, 1H), 2.60 (t, J=5.61 Hz, 1H), 2.72 (t, J=5.86 Hz, 1H), 2.84-2.96 (m, 2H), 3.26-3.32 (m, 2H), 3.56 (dt, J=8.79, 5.13 Hz, 1H), 3.65-3.78 (m, 3H), 3.81-3.94 (m, 2H), 4.33-4.47 (m, 3H), 4.52 (tt, J=8.18, 4.03 Hz, 1H), 5.91 (dd, J=13.42, 6.10 Hz, 1H), 6.97-7.05 (m, 1H), 7.24-7.36 (m, 2H); ESI-MS m/z [M+H]$^+$ 474; mp 150° C. (DSC peak); chiral purity (via chiral column chromatography)>98% ee.

Compound A: (S)-1-(2-(4-(2,4-difluorophenoxy)piperidin-1-yl)-3-((tetrahydrofuran-3-yl)amino)-7,8-dihydropyrido[3,4-b]pyrazin-6(5H)-yl)ethan-1-one

A

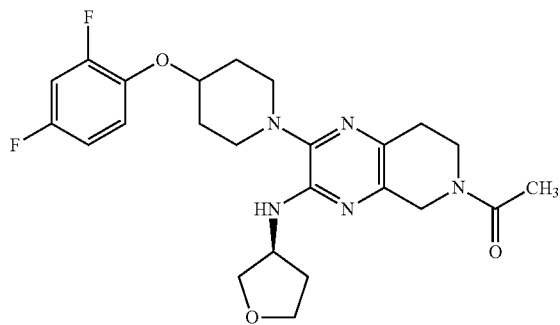

To a flask charged with (S)-2-(4-(2,4-difluorophenoxy)piperidin-1-yl)-N-(tetrahydrofuran-3-yl)pyrido[3,4-b]pyrazin-3-amine (1.05 g, 2.456 mmol) in HOAc (5 mL) and THF (5 mL) under nitrogen was added acetic anhydride (1.159 mL, 12.28 mmol). Palladium on carbon (10%, Aldrich 205699-10G, Lot #MKBZ3284V) (0.523 g, 0.491 mmol) was added under nitrogen. The flask was connected to a hydrogen-filled balloon and was evacuated with house vacuum and refilled with hydrogen eight times. The reaction mixture was stirred under hydrogen for 18 hours and then filtered through a pad of Celite®, taking care not to let the cake dry out. The flask and filter cake were rinsed with EtOAc (20 mL), methanol (20 mL) and EtOAc (20 mL) and the filtrate was concentrated in vacuo on CELITE®. The crude product was purified by column chromatography (120 g NH silica gel column, size 200) eluting with a gradient of 0 to 60% EtOAc in heptane to give a white solid (1.0 g). The white solid was taken up in ethanol (5 mL) and heated to 80° C. in an oil bath with stirring. After the solids were dissolved, heating was discontinued, and the solution was allowed to cool slowly in the oil bath to 20° C. with stirring. The mixture was stirred for 3 days at room temperature. The solids were collected by vacuum filtration, rinsed with ice-cold ethanol, and dried under high vacuum to give the title compound as a white solid (848 mg, 72.9%). $^1$H NMR (500 MHz, DMSO-$d_6$) δ ppm 1.82-2.00 (m, 3H), 2.02-2.12 (m, 5H), 2.13-2.24 (m, 1H), 2.60 (t, J=5.86 Hz, 1H), 2.72 (t, J=5.86 Hz, 1H), 2.83-2.96 (m, 2H), 3.24-3.32 (m, 2H), 3.56 (dt, J=8.79, 5.25 Hz, 1H), 3.66-3.77 (m, 3H), 3.81-3.94 (m, 2H), 4.33-4.47 (m, 3H), 4.52 (tt, J=8.08, 3.87 Hz, 1H), 5.93 (dd, J=13.30, 6.22 Hz, 1H), 6.98-7.06 (m, 1H), 7.24-7.35 (m, 2H); ESI-MS m/z [M+H]$^+$ 474; mp 149° C. (DSC peak); chiral purity (via chiral column chromatography)>98% ee.

IV. In Vitro Inhibition of cAMP ($EC_{50}$) Assay

Table 1 lists biological assay data (in vitro inhibition of cAMP) for the compound of Formula 1 (Example 1) and Compound A, which were tested in accordance with a cell-based assay which measures the ability of test compounds to inhibit the constitutive cAMP activity of GPR6 receptor expressed in CHO-K1 cells (reported as $pEC_{50}$). The assay is described in the specification under the heading "In vitro inhibition of cAMP ($EC_{50}$)."

TABLE 1

| In vitro Inhibition of Constitutive cAMP Activity of GPR6 Receptor | |
|---|---|
| Compound | $pEC_{50}$ |
| Formula 1 | 7.2 |
| Compound A | 7.2 |

Further analysis is performed by determining the $IC_{50}$ of the compounds using the assay described in the specification under the heading "In vitro inhibition of cAMP ($IC_{50}$)".

V. In Vitro Inhibition of cAMP ($IC_{50}$) Assay

Table 2 lists the inhibition constant (Ki) from a GPR6 competition binding assay and the $IC_{50}$ values from a hERG functional assay for the compound of Formula 1 (Example 1) and for Compound A. As described above, Ki for each compound was obtained using a competition binding assay which employed a filtration-based format utilizing membranes prepared from CHO-K1 cells expressing human GPR6 cDNA; $IC_{50}$ for each compound was obtained using a hERG functional assay which employed an automated whole cell patch-clamp system utilizing CHO-K1 cells transfected with human hERG cDNA.

The data in Table 2 indicate the compound of Formula 1 is a significantly less potent inhibitor of hERG than Compound A. If one assumes 50% occupancy of GPR6 at maximum free compound (drug) concentration, then the ratio (hERG $IC_{50}$)/Ki shown in Table 2 may be viewed as a safety margin for the free drug ("SM-free") as defined in the literature (see X. Yao et al., *British Journal of Pharmacology* (2008) 154:1446-56, 50, which is hereby incorporated by reference in its entirety). Comparing safety margins, the compound of Formula 1 exhibits improved SM-free for progressing into in vivo studies. An SM-free of less than 300 is considered appropriate to progress into in vivo studies, as defined in Yao et al at page 1452 ("findings suggest that an SM-free of 300 or more may denote a compound devoid of a potential for causing QTc prolongation").

TABLE 2

GPR6 Competition Binding (Ki) and hERG Inhibition ($IC_{50}$)

| Compound | Ki (nM) | $IC_{50}$ (nM) | (hERG $IC_{50}$)/Ki |
|---|---|---|---|
| Formula 1 | 5.5 | 1970 | 358 |
| Compound A | 6.0 | 505 | 84 |

The ability of the compound of Formula 1 (Example 1) and Compound A to reverse haloperidol-induced catalepsy is also analyzed. The compounds are tested in accordance with the assay described in the disclosure under the heading "In vivo Parkinson's Disease Model—Haloperidol-induced Catalepsy."

VI. Treatment of the 6-Hydroxydopamine (6-OHDA) Rat Model

Compounds that improve motor activity are considered promising as potential therapies for Parkinson's disease. Rats of the 6-OHDA model of Parkinson's disease received bilateral injections of 6-OHDA into the striatum and coordinates Anterior-Posterior (AP): Medial-Lateral (ML): Dorsal-Ventral (DV), 1±3, −5 mm relative to Bregma under anaesthesia. Rats were tested for locomotor activity at least 28 days later. Animals were habituated for 30 minutes in locomotor activity boxes prior dosing with Formula 1 (Example 1) or the vehicle (control).

Locomotor activity was measured in an open field arena covered in an array of infrared beams. Beam breaks by the animals were processed using AMLOGGER software to monitor activity. Formula 1 (Example 1) showed a dose dependent improvement in locomotor activity for both dosages (5 mg/kg and 10 mg/kg) compared to rats administered the vehicle (control) after 50 minutes as shown in FIG. 1. A significant increase in activity was observed in rats administered the 10 mg/kg dose. These data indicate that Formula 1 (Example 1) will be effective in improving the symptoms of Parkinson's disease patients.

VII. Effects of Formula 1 (Example 1) on the Cardiovascular System Using Telemetry The potential cardiovascular effects of Formula 1 (Example 1) in conscious beagle dogs (Marsahall BioResources, North Rose, N.Y.) for a minimum of 8 months of age and weighing 7-15 kg. The beagle dogs are equipped with telemetry devices from DSI PHYSIOTEL® Digital L21 transmitter implants according to the appropriate Charles River Laboratories, Montreal, QC Standard Operating Procedure (TB 12-04-06). The biopotential leads are placed in a modified lead II configuration. A minimum acclimation period of 6 days is allowed between animal arrival and the start of the surgical implantation of the telemetry devices in order to accustom the animals to the laboratory environment. A minimum recovery period of 4 weeks is allowed between surgeries and the start of treatment. The targeted conditions for animal room environment are between 17° C. and 23° C. at 30-70% humidity with 12 hours of light and 12 hours of dark, except during designated procedures.

Animals may be socially housed in stainless steel cages equipped with an automatic watering valve as described in the *Guide for the Care and Use of Laboratory Animals* (8th Ed., National Academies Press, 2111), which is hereby incorporated by reference in its entirety, with the exception of dosing and monitoring periods where animals are individually housed.

Following surgical implantation of the DSI PHYSIO-TEL® Digital L21 transmitters, animals receive food supplementation for 7 days following surgery which consist of 1 can of AID Prescription Diet mixed with 300 g of PMI NUTRITION® International Certified Canine Chow No. 5007 for 3 days, and 1 can of AID Prescription Diet mixed with 300 g of PMI NUTRITION® International Certified Canine Chow No. 5007 for 4 days. On the day of dosing, food is provided at least 5 hours prior to the start of dosing, made available for a target of 1 hour, and then removed at least 4 hours prior to dosing. Beefy treats are not available after the food is removed during the 4-hour period prior to dosing. The remaining food, if any, is offered during the end of the day's mortality/moribundity checks and is left overnight. Supplemental diet is provided to the animals as warranted by clinical signs or other changes.

Municipal tap water after treatment by reverse osmosis and ultraviolet irradiation is freely available to each animal via an automatic watering system, except during designated procedures. Water bowls are provided, if required. Periodic analysis of the water is performed, and results of these analyses are on file at the Test Facility. No known contaminants that could interfere with the objectives of the study are considered to be present in the water.

Prior to the start of dosing, ECGs, LVP, blood pressure and body temperature are collected using Data Sciences International (DSI) PONEMAH™ system for at least 24 hours to evaluate cardiovascular parameters and ECG signal quality. ECGs of a minimum of 30 seconds duration are collected and sent to a cardiologist for qualitative review. Only animals exhibiting normal hematology/clinical chemistry parameters and normal hemodynamic/ECG parameters are enrolled into the study.

Animals are acclimated to the oral gavage procedure for at least 3 days prior to the commencement of dose formulation administration. Cage/tap water are administered by oral gavage using a disposable catheter attached to a plastic syringe at a dose volume of 5 mL/kg. The dosing formulations are stirred for at least 30 minutes in the animal room prior to and continuously during dose administration.

A single dose of vehicle (control), which contains 2% Lecithin and 0.5% Methylcellulose in ULTRAPURE™ Water (Charles River Laboratories, Montreal, QC) or test compound at 30, 100 and 300 mg/kg is administered by oral gavage. The vehicle is prepared for each dose session and stored in a refrigerator maintained at 4° C., on stir plate, protected from light, and dispensed as required. Vehicle is removed from the refrigerator and stirred for at least 30 minutes at room temperature before dosing and continuously during dosing. The dosing formulations are stored in a refrigerator set at 4° C., on a stir plate, protected from light, and dispensed as required. The dosing formulations are removed from the refrigerator, stirred for at least 30 minutes at room temperature before dosing and continuously during dosing.

Each of four male dogs receives a dose of vehicle and three dose levels of Formula 1 (Example 1) with 7 days between each dose. The parameters monitored include: heart rate derived from blood pressure, left ventricular pressure (LVP), and electrocardiogram waveforms; LVP (peak systolic and end-diastolic LVP and max positive/negative dP/dt values); electrocardiogram (PR interval (PR), RR variability (RR"), QRS complex (QRS), QT intervals, and QTcv calculated using the Van de Water equation QTcv=QT−87(60/HR−1)); and body temperature.

Marking of ECG segments is conducted using ECG Pattern Recognition software. A library for each animal is constructed of representative cycles from both the day and night cycle and is applied across monitoring occasions to ensure appropriate marking for quantitative assessments, in accordance with the appropriate Charles River Laboratories, Montreal, QC. Any data values which exceed the electrophysiological norms for this species is excluded from further analysis.

During each telemetry monitoring occasion on dosing days, ECG is evaluated twice prior to each dose (at least 30 minutes apart) and at approximately 1 (±5 minutes), 2, 4, 6, 8, 10, 12, 15, 18, and 23 (±15 minutes) hours post dose. A minimum of 30 seconds is evaluated at each timepoint. All waveforms are qualitatively evaluated to detect rhythm or conduction disturbances or other abnormalities of the P-QRS-T waves. Blood samples are collected from the jugular vein, following overnight food deprivation (for clinical chemistry).

No changes are observed in beagle dogs administered the compound of Formula 1 (Example 1) compared to results from the vehicle in arterial blood pressures, contractility or P-R interval, QRS complex, or QT interval durations for animals dosed with Formula 1 (Example 1).

EQUIVALENTS AND SCOPE

Those skilled in the art will recognize or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. The present invention is further illustrated by the non-limiting examples herein.

What is claimed is:

1. A compound of Formula 1,

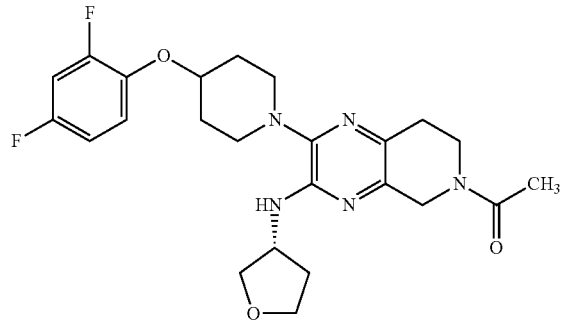

or a pharmaceutically acceptable salt thereof.

2. The compound or pharmaceutically acceptable salt according to claim 1, which has an enantiomeric purity equal to or greater than 20% enantiomeric excess (ee).

3. The compound or pharmaceutically acceptable salt according to claim 1, which has an enantiomeric purity equal to or greater than 40% enantiomeric excess (ee).

4. The compound or pharmaceutically acceptable salt according to claim 1, which has an enantiomeric purity equal to or greater than 60% enantiomeric excess (ee).

5. The compound or pharmaceutically acceptable salt according to claim 1, which has an enantiomeric purity equal to or greater than 80% enantiomeric excess (ee).

6. The compound or pharmaceutically acceptable salt according to claim 1, which has an enantiomeric purity equal to or greater than 90% enantiomeric excess (ee).

7. The compound or pharmaceutically acceptable salt according to claim 1, which has an enantiomeric purity equal to 100% enantiomeric excess (ee).

8. The compound or pharmaceutically acceptable salt according to claim 1, wherein the compound is present as a free form.

9. A pharmaceutical composition comprising:
   (a) a compound or pharmaceutically acceptable salt according to claim 1; and
   (b) a pharmaceutically acceptable excipient.

10. A method of treating a disease, disorder or condition associated with GPR6 in a subject, the method comprising administering to the subject a compound or pharmaceutically acceptable salt thereof according to claim 1; wherein the disease, disorder, or condition is at least one selected from the group consisting of: Parkinson's disease, levodopa-induced dyskinesias, Huntington's disease, drug addiction, eating disorders, cognitive disorders, schizophrenia, bipolar disorder, epilepsy, Alzheimer's disease, anxiety, and depression.

11. The method according to claim 10, wherein the compound or pharmaceutically acceptable salt is administered at a dose within a range selected from the group consisting of about 30 mg/kg to about 40 mg/kg, about 35 mg/kg to about 45 mg/kg, about 40 mg/kg to about 50 mg/kg, about 45 mg/kg to about 55 mg/kg, about 50 mg/kg to about 60 mg/kg, about 55 mg/kg to about 65 mg/kg, and about 60 mg/kg to about 70 mg/kg.

12. The method according to claim 10, wherein the compound or pharmaceutically acceptable salt is administered at a dose of about 50 mg/kg.

13. The method according to claim 10, wherein the administering step occurs perorally.

14. A combination therapy comprising the pharmaceutical composition according to claim 9, and at least one additional pharmacologically active agent selected from the group consisting of: levodopa, a DOPA decarboxylase inhibitor, a dopamine agonist, an anticholinergic, a B-selective monoamine oxidase inhibitor, and a catechol O-methyl transferase inhibitor.

15. The combination therapy according to claim 14, wherein the additional pharmacologically active agent is amantadine.

16. The combination therapy according to claim 14, wherein the additional pharmacologically active agent is levodopa in combination with a DOPA decarboxylase inhibitor.

17. The combination therapy according to claim 14, wherein the additional pharmacologically active agent is selected from the group consisting of: carbidopa; benserazid; methyldopa; α-difluoromethyl-DOPA; 3',4',5,7-tetrahydroxy-8-methoxyisoflavone; apomorphine hydrochloride; bromocriptine; rotigotine; pramipexole; ropinirole; trihexyphenidyl; benztropine mesylate; safinamide; selegiline; rasagiline; entacapone; and tolcapone.

18. The combination therapy of claim 14, wherein the additional pharmacologically active agent is selected from the group consisting of: beta-secretase inhibitors, gamma-secretase inhibitors, HMG-CoA reductase inhibitors, nonsteroidal anti-inflammatory drugs (NSAIDs).

19. The combination therapy of claim 18, wherein the nonsteroidal anti-inflammatory drug (NSAID) is selected from the group consisting of: apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac.

20. The combination therapy of claim 14, wherein the additional pharmacologically active agent is selected from the group consisting of: donepezil, rivastigmine, memantine, and galantamine.

21. The combination therapy of claim 14, wherein the additional pharmacologically active agent is selected from the group consisting of: sedatives, hypnotics, anxiolytics, antipsychotics, and tranquilizers.

22. The combination therapy of claim 14, wherein the additional pharmacologically active agent is selected from the group consisting of: amitriptyline, amoxapine, aripiprazole, asenapine, bupropion, chlordiazepoxide, citalopram, chlorpromazine, clozapine, desipramine, desvenlafaxine, doxepin, duloxetine, escitalopram, fluoxetine, fluoxetine, fluphenazine, haloperidol, iloperidone, imipramine, isocarboxazid, lamotrigine, levomilnacipran, lurasidone, mirtazapine, nefazodone, nortriptyline, olanzapine, paliperidone, paroxetine, perphenazine, phenelzine, protriptyline, quetiapine, risperidone, safinamide, selegiline, sertraline, tranylcypromine, trazodone, trimipramine, venlafaxine, vilazodone, vortioxetine, and ziprasidone.

23. The combination therapy of claim 14, wherein the additional pharmacologically active agent is selected from the group consisting of: alprazolam, chlordiazepoxide, clobazepam, clonazepam, clorazepate, diazepam, estazolam, flurazepam, lorazepam, midazolam, oxazepam, prazepam, quazepam, temazepam, and triazolam, hydroxyzine, eszopiclone, zaleplon, zolpidem, and zopiclone, and buspirone.

24. The combination therapy of claim 14, wherein the additional pharmacologically active agent is selected from the group consisting of: acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

25. A dosage form comprising a compound or pharmaceutically acceptable salt thereof according to claim 1 and a pharmaceutically acceptable excipient, wherein the dosage form is adapted for oral administration of the compound or pharmaceutically acceptable salt thereof at a dose selected from the group consisting of: 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 61 mg/kg, 62 mg/kg, 63 mg/kg, 64 mg/kg, and 65 mg/kg.

26. The dosage form of claim 25, wherein the dose is 50 mg/kg.

27. The method according to claim 10, wherein the compound or pharmaceutically acceptable salt thereof is administered at a total daily dose selected from a range of about 0.1 mg/kg to about 1.0 mg/kg or about 0.5 mg/kg to about 5.0 mg/kg.

28. A dosage form comprising a compound or pharmaceutically acceptable salt thereof according to claim 1, wherein the dosage form is adapted for oral administration of the compound or pharmaceutically acceptable salt thereof at a total daily dose selected from a range of about 0.1 mg/kg to about 1.0 mg/kg or about 0.5 mg/kg to about 5.0 mg/kg.

* * * * *